United States Patent
Sato et al.

(10) Patent No.: US 9,142,208 B2
(45) Date of Patent: Sep. 22, 2015

(54) ULTRASONIC PROBE AND ULTRASONIC DIAGNOSTIC EQUIPMENT USING SAME

(75) Inventors: Toshiharu Sato, Tokyo (JP); Eiichi Ookawa, Kanagawa (JP)

(73) Assignee: KONICA MINOLTA, INC., Tokyo (JP)

(*) Notice: Subject to any disclaimer, the term of this patent is extended or adjusted under 35 U.S.C. 154(b) by 219 days.

(21) Appl. No.: 13/320,472

(22) PCT Filed: May 14, 2010

(86) PCT No.: PCT/JP2010/003270
§ 371 (c)(1),
(2), (4) Date: Nov. 14, 2011

(87) PCT Pub. No.: WO2010/131479
PCT Pub. Date: Nov. 18, 2010

(65) Prior Publication Data
US 2012/0065515 A1     Mar. 15, 2012

(30) Foreign Application Priority Data
May 14, 2009   (JP) .................. 2009-117484

(51) Int. Cl.
*G10K 11/35*   (2006.01)
*A61B 8/12*    (2006.01)
*A61B 8/00*    (2006.01)

(52) U.S. Cl.
CPC .............. *G10K 11/355* (2013.01); *A61B 8/12* (2013.01); *A61B 8/4461* (2013.01)

(58) Field of Classification Search
CPC ............. A61B 8/4461; A61B 2019/2246; G10K 11/355; G10K 11/352; G01S 15/8938; F16H 55/36; F16H 57/0006; B65H 2403/20; B65H 2404/733

USPC ............................. 600/444, 445, 472
See application file for complete search history.

(56) References Cited

U.S. PATENT DOCUMENTS

| 2,347,900 | A  | * | 5/1944  | Frazer-Nash et al. | 74/98    |
|-----------|----|---|---------|--------------------|----------|
| 3,298,272 | A  | * | 1/1967  | Henderson          | 411/373  |
| 4,073,250 | A  | * | 2/1978  | Kasuga             | 112/274  |
| 4,295,621 | A  | * | 10/1981 | Siryj              | 248/183.2|
| 4,411,182 | A  | * | 10/1983 | Borzym             | 83/319   |
| 4,913,158 | A  | * | 4/1990  | Kikuchi et al.     | 600/446  |
| 6,045,212 | A  | * | 4/2000  | Ruhe et al.        | 347/37   |
| 2002/0062080 | A1 | * | 5/2002  | Okawa et al.    | 600/459  |
| 2005/0109274 | A1 | * | 5/2005  | Kitano et al.   | 118/684  |
| 2006/0173330 | A1 | * | 8/2006  | Kim             | 600/445  |

FOREIGN PATENT DOCUMENTS

| JP | 2002-153464 | 5/2002  |
| JP | 2006-187592 | 7/2006  |
| JP | 2006-320476 | 11/2006 |

* cited by examiner

*Primary Examiner* — Long V Le
*Assistant Examiner* — Ellsworth Weatherby
(74) *Attorney, Agent, or Firm* — Lucas & Mercanti, LLP (57) ABSTRACT

An ultrasonic diagnostic equipment of the present invention includes: an ultrasonic transducer body transmitting and receiving ultrasonic waves; a swing shaft (4) attached integrally to the ultrasonic transducer body; a swing shaft pulley (5) provided on the swing shaft; a motor having an output shaft (7); an output shaft pulley (8) provided on the output shaft; a belt (9) wound around the swing shaft pulley and the output shaft pulley; a plurality of belt fixing screws (11, 12) fixing the belt to the swing shaft pulley and the output shaft pulley. The belt is divided into two regions at the belt fixing screws so as to allow the regions to have different natural frequencies.
With this configuration, it is possible to provide a highly reliable ultrasonic probe and an ultrasonic diagnostic equipment using the ultrasonic probe.

20 Claims, 6 Drawing Sheets

ND ULTRASONIC
ULTRASONIC PROBE AND ULTRASONIC DIAGNOSTIC EQUIPMENT USING SAME

TECHNICAL FIELD

The present invention relates to an ultrasonic probe utilized in medical fields such as an ultrasonic diagnosis, a treatment and the like, in particular, to an ultrasonic probe having a function of swinging ultrasonic transducers mechanically, and an ultrasonic diagnostic equipment using the ultrasonic probe.

BACKGROUND ART

An ultrasonic probe composed of a plurality of piezoelectric transducers arranged so that an ultrasonic wave sending/receiving face forms a convex shape has been known conventionally (for example, see Patent Document 1). The ultrasonic probe can obtain a plurality of tomographic images and construct three-dimensional images by electronic scanning that is performed in an arrangement direction of the piezoelectric transducers (electronic scanning direction) and mechanical scanning that causes the piezoelectric transducers to move or swing in a direction different from the electronic scanning direction.

Figure 7:
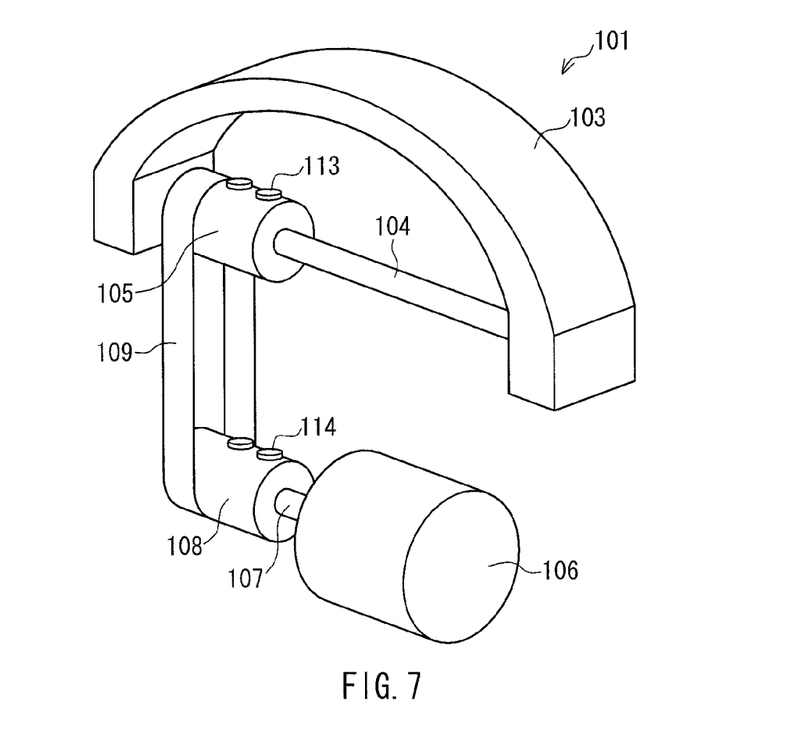
FIG. 7 is a perspective view showing a configuration of a conventional ultrasonic probe.

FIG. 7 is a perspective view showing a configuration of such an ultrasonic probe 101. An ultrasonic transducer body 103 has a plurality of piezoelectric transducers (not shown) arranged so as to form a convex shape, and transmits and receives ultrasonic waves. A swing shaft 104 is fixed to the ultrasonic transducer body 103, and supported swingably by a supporter (not shown). The swing shaft 104 is inserted in a swing shaft pulley 105, which is fixed to the swing shaft 104 by a pulley fastening screw 113. Further, an output shaft 107 of a motor 106 as a driving source is inserted in an output shaft pulley 108, which is fixed to the output shaft 107 by a pulley fastening screw 114. A belt 109 is wound around the swing shaft pulley 105 and the output shaft pulley 108.

The forward-backward rotation motion of the motor 106 is transmitted to the output shaft pulley 108, the belt 109, and the swing shaft pulley 105 in this order, which causes the ultrasonic transducer body 103 to swing around the swing shaft 104. By this motion, mechanical scanning by the swing of the ultrasonic transducer body 103 around the swing shaft 104 can be performed. Therefore, by combining the mechanical scanning with the electronic scanning performed by the plurality of the piezoelectric transducer arrays constituting the ultrasonic transducer body 103, it is possible to obtain certain tomographic images of a subject (not shown) and construct three-dimensional images.

PRIOR ART DOCUMENT

Patent Document

[Patent Document 1] JP 2006-320476 A

DISCLOSURE OF INVENTION

Problem to be Solved by the Invention

In the mechanical scanning, when the output shaft 107 rotates forward or backward, the output shaft pulley 108 rotates forward or backward. The belt frequently repeats forward-backward motion along with the forward-backward rotation of the output shaft pulley 108.

Since the conventional belt 109 is formed entirely of the same material in the same width and the same thickness, two regions in the belt 109, which are divided at the swing shaft pulley 105 and the output shaft pulley 108, have the same natural frequency. With this configuration, a resonance phenomenon may occur in the belt 109 due to tension and slack of the belt 109 attributed to a swing cycle. When the resonance phenomenon occurs, the swing motion becomes erratic and the probe vibrates more, which makes it difficult to capture highly reliable ultrasonic images.

Further, since the ultrasonic probe is operated by being held by an operator's hand, the ultrasonic probe is required to be formed smaller and lighter. The swing shaft pulley 105 and the output shaft pulley 108 are fixed to the swing shaft 104 and the output shaft 107 by the pulley fastening screws 113 and 114, respectively. In other words, in order to secure places for attaching the pulley fastening screws 113, 114, widths of the swing shaft pulley 105 and the output shaft pulley 108 need be larger than a width of the belt 109. For making the ultrasonic probe smaller and lighter, it is desirable that the widths of the pulleys 105, 108 be substantially the same as the width of the belt 109.

However, when the belt 109 and the pulleys 105, 108 have substantially the same width, the pulley fastening screws 113, 114 come into contact with the belt 109. When a screw having a screw head protruding further than a circumferential surface of the pulley (e.g., pan-head machine screw) is used as the pulley fastening screws 113, 114, the belt 109 runs upon the pulley fastening screws 113, 114, which makes it difficult for the ultrasonic transducer body 103 to perform an accurate swing motion.

On the other hand, when a screw having a screw head not protruding from the circumferential surface of the pulley (e.g., flat-head machine screw, hexagon socket set screw) is used as the pulley fastening screws 113, 114, the belt 109 does not run upon the screws; however, it is positioned on the screw holes. The belt 109 may be damaged and in some cases fractured due to repetitive sliding contact with edges of the screw holes. Although there also are methods of fixing the pulley to the shaft such as press fitting and adhesive fixing without using the pulley fastening screws 113, 114, such methods decrease the ability to disassemble the shaft and the pulley, which interferes with adjustment, repair, etc.

The present invention is made to solve the above-described conventional problems, and it is an object of the present invention to provide an ultrasonic probe capable of stabilizing the swing motion by suppressing the occurrence of a resonance phenomenon of a belt and an ultrasonic diagnostic equipment using the ultrasonic probe.

It is another object of the present invention to downsize a width of a pulley to a size equivalent to a width of a belt.

It is another object of the present invention to maintain the capability of disassembling a shaft and a pulley while achieving the above-described objects.

Means for Solving Problem

In order to solve the above-described conventional problems, a first ultrasonic probe of the present invention includes: an ultrasonic transducer body transmitting and receiving an ultrasonic wave; a swing shaft attached integrally to the ultrasonic transducer body; a swing shaft pulley provided on the swing shaft; a motor having an output shaft; an output shaft pulley provided on the output shaft; a belt wound around the swing shaft pulley and the output shaft pulley; and a plurality of belt fixing screws fixing the belt to the swing shaft pulley and the output shaft pulley. The belt is divided into two regions at the belt fixing screws so as to allow the regions to have different natural frequencies.

As described above, by differentiating the natural frequency between the two regions in the belt, the belt can be suppressed from resonating. Thereby the reliability of the ultrasonic probe is increased and the quality of an ultrasonic image is improved particularly.

Further, in order to solve the above-described conventional problems, a second ultrasonic probe of the present invention includes: an ultrasonic transducer body transmitting and receiving an ultrasonic wave; a swing shaft attached integrally to the ultrasonic transducer body; a swing shaft pulley provided on the swing shaft; a motor having an output shaft; an output shaft pulley provided on the output shaft; an intermediate shaft provided rotatably; a first intermediate shaft pulley and a second intermediate shaft pulley provided on the intermediate shaft; a first belt wound around the swing shaft pulley and the first intermediate shaft pulley; a second belt wound around the second intermediate shaft pulley and the output shaft pulley; and a plurality of fastening screws fixing the first belt and the second belt to their respective pulleys. Each of the first belt and the second belt is divided into two regions at the fastening screws so as to allow the regions to have different natural frequencies.

As described above, by differentiating the natural frequency between the two regions in the belt, the belt can be suppressed from resonating. Thereby the reliability of the ultrasonic probe is increased and the quality of an ultrasonic image is improved particularly.

Further, the first and the second ultrasonic probes can be configured such that the two regions in the belt have different natural frequencies by differentiating a material weight of the regions.

Further, it is possible to have a configuration that further includes a pulley fastening screw that fixes each of the pulleys to the shaft to which the pulley is attached, wherein the pulley fastening screw is inserted completely in a screw hole, and a screw hole filler is placed over the pulley fastening screw so as to fill the screw hole. With this configuration, it is possible to prevent the belt from being damaged by contacting an edge of the screw hole.

Further, it is possible to have a configuration in which the two regions in the belt have different natural frequencies by forming a through hole in one of the regions.

Further, it is possible to have a configuration in which a cross belt configuration is formed by passing the other region through the through hole. With this configuration, a contact area between the belt and the pulleys becomes large, thereby transmitting a driving force between the pulleys and the belt reliably and performing a more stable swing motion.

Further, it is possible to have a configuration that further includes a pulley fastening screw that fixes each of the pulleys to the shaft to which the pulley is attached, at a portion of the pulley where the through hole is positioned when the pulley rotates. With this configuration, the belt does not contact the pulley fastening screw, which makes it possible to prevent the belt from being damaged.

Further, it is possible to have a configuration in which the pulley fastening screw is inserted completely in a screw hole, and a screw hole filler is placed over the pulley fastening screw so as to fill the screw hole. With this configuration, it is possible to prevent the belt from being damaged by contacting an edge of the screw hole.

Further, it is possible to have a configuration in which a pulley fastening screw that fixes each of the pulleys to the shaft to which the pulley is attached is inserted in a bottom of a screw hole of the belt fixing screw. With this configuration, the pulley can be fixed to the shaft without providing another screw hole. Thus, the fixation of the pulley to the shaft can be performed reliably.

It is possible to have a configuration in which a width of each of the pulleys is the same as a width of the belt. With this configuration, the ultrasonic probe can be formed smaller and lighter.

In order to solve the above-described conventional problems, an ultrasonic diagnostic equipment of the present invention includes: the above-described ultrasonic probe; and an ultrasonic diagnostic equipment main body connected electrically to the ultrasonic probe. With this configuration, it is possible to provide an ultrasonic diagnostic equipment having the effects of the above-described ultrasonic probe and capable of obtaining favorable ultrasonic diagnostic images efficiently.

Effect of the Invention

According to the present invention, by differentiating the natural frequency between the two regions in the belt that are divided at the belt fixing screws, it is possible to provide a highly reliable ultrasonic probe suppressing the occurrence of the resonance phenomenon and securing the stable motion, and an ultrasonic diagnostic equipment using the ultrasonic probe.

Further, by equalizing the widths of the pulley and the belt, it is possible to downsize the ultrasonic probe.

Further, by fixing the pulleys and the belt using screws, it is possible to maintain the ability to disassemble the pulleys and the belt.

DESCRIPTION OF EMBODIMENTS

Hereinafter, an ultrasonic probe and an ultrasonic diagnostic equipment according to embodiments of the present invention will be described with reference to the drawings.

(Embodiment 1)

Figure 1:
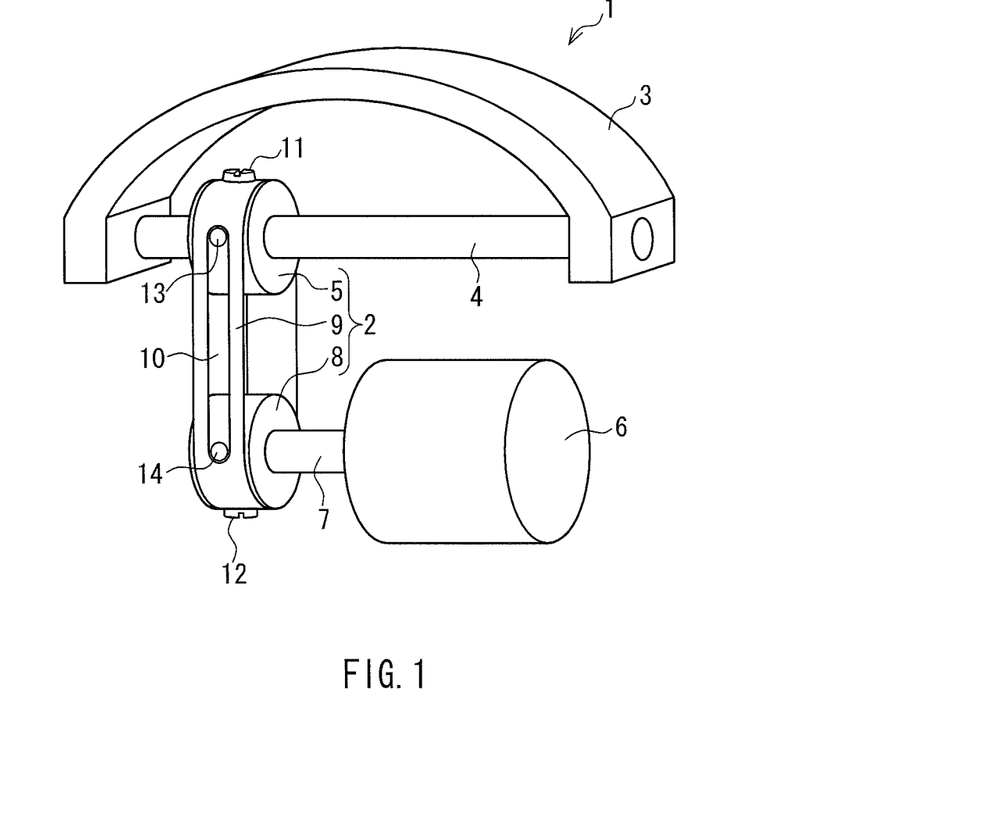
FIG. 1 is a perspective view showing a configuration of main portions of an ultrasonic probe according to Embodiment 1 of the present invention.

FIG. 1 is a perspective view showing a configuration of main portions inside an ultrasonic probe 1 according to Embodiment 1 of the present invention. An ultrasonic transducer body 3 is composed of a plurality of piezoelectric transducers (not shown) arranged so that a sending/receiving face forms a convex shape. The ultrasonic transducer body 3 transmits ultrasonic waves with respect to a subject and receives reflected waves from the subject. A swing shaft 4 is joined integrally with the ultrasonic transducer body 3 on an opposite side relative to the ultrasonic wave sending/receiving face of the ultrasonic transducer body 3, and supported swingably by a supporter (not shown).

A motion transmission mechanism 2 is composed of the swing shaft 4, a swing shaft pulley 5, an output shaft 7, an output shaft pulley 8 and a belt 9, and transmits a driving force of a motor 6 so as to swing the ultrasonic transducer body 3. A through hole 10 is formed in a part of the belt 9. The swing shaft 4 is inserted in the swing shaft pulley 5, which is fixed to the swing shaft 4 by a pulley fastening screw 13.

The motor 6 as a driving source has the output shaft 7 as a rotation shaft, and is fixed to a supporter (not shown). The output shaft 7 is inserted in the output shaft pulley 8, which is fixed to the output shaft 7 by a pulley fastening screw 14.

The belt 9 is wound around the swing shaft pulley 5 and the output shaft pulley 8. The belt 9 is fixed to the swing shaft pulley 5 by a belt fixing screw 11 on the swing shaft side, and fixed to the output shaft pulley 8 by a belt fixing screw 12 on the output shaft side. A width of the belt 9 substantially is the same as widths of the swing shaft pulley 5 and the output shaft pulley 8. In order to avoid having the belt 9 contact edges of the swing shaft pulley 5 and output shaft pulley 8, it is preferable that the swing shaft pulley 5 and the output shaft pulley 8 are slightly wider than the belt 9.

In the ultrasonic probe configured as above, driving the motor 6 causes the output shaft 7 to rotate, the rotation then being transmitted to the output shaft pulley 8, the belt 9, the swing shaft pulley 5 and the swing shaft 4. Along with the rotation of the swing shaft 4, the ultrasonic transducer body 3 joined integrally with the swing shaft 4 swings, thereby transmitting and receiving ultrasonic waves at an appropriate position. Mechanical scanning is performed by the repetition of the above.

Figure 2A:
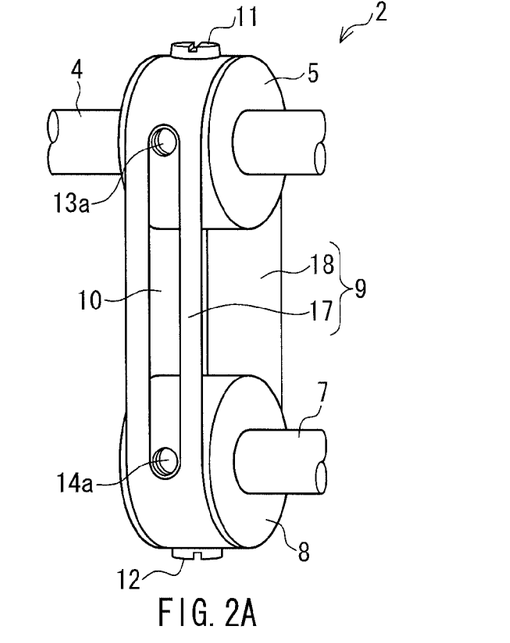
FIG. 2A is a perspective view showing a configuration of a motion transmission mechanism of the ultrasonic probe according to the present embodiment.
Figure 2B:
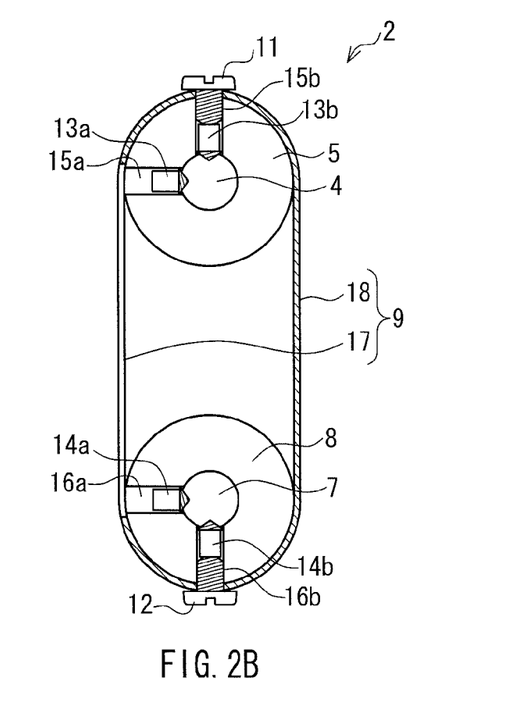
FIG. 2B is a cross-sectional view of the motion transmission mechanism shown in FIG. 2A.

Next, the motion transmission mechanism 2 of the ultrasonic probe composed of the swing shaft 4, the output shaft 7, the swing shaft pulley 5, the output shaft pulley 8 and the belt 9 will be described in more detail. FIG. 2A is a perspective view showing a configuration of the motion transmission mechanism of the ultrasonic probe according to the present embodiment, and FIG. 2B is a cross-sectional view of the motion transmission mechanism 2 of FIG. 2A.

The belt 9 is formed of a metallic sheet material such as stainless steel. A flexible material such as rubber also can be used as the belt 9. However, in this case, a swing speed and a swing angle of the ultrasonic transducer body 3 may vary due to the extension-retraction of the belt 9. Therefore, in order to suppress the variations in the swing speed and the swing angle and to cause the ultrasonic transducer body 3 to swing accurately, it is preferable that the belt 9 is made of metal such as stainless steel.

The belt 9 is fixed to the swing shaft pulley 5 by the belt fixing screw 11 on the swing shaft side, and fixed to the output shaft pulley 8 by the belt fixing screw 12 on the output shaft side. As shown in FIG. 2B, the belt 9 is divided into two regions on the left and right (a first region 17 and a second region 18) at the attachment portions (locations) of the belt fixing screws 11, 12. The first region 17 and the second region 18 in the belt 9 are configured to have different natural frequencies. In the present embodiment, by forming the through hole 10 in the first region 17, the first region 17 becomes lighter than the second region 18, which provides a difference in natural frequency. With this configuration, the belt 9 can be suppressed from resonating when moving forward and backward.

The type and the length of the pulley fastening screws 13, 14 are such that they do not have screw heads (e.g., hexagon socket set screw) and are contained inside screw holes. The swing shaft pulley 5 is fixed to the swing shaft 4 by two pulley fastening screws 13a, 13b. Further, the output shaft pulley 8 is fixed to the output shaft 7 by two pulley fastening screws 14a, 14b.

The motion transmission mechanism is required to transmit a driving force applied to the output shaft 7 to the swing shaft 4 reliably. If the output shaft pulley 8 is not fixed to the output shaft 7 sufficiently, the driving force cannot be transmitted to the belt 9 sufficiently. Further, in order to transmit the driving force transmitted to the belt 9 to the swing shaft 4 sufficiently, the swing shaft pulley 5 should be fixed to the swing shaft 4 reliably. Therefore, the pulley fastening screws 13, 14, each fixing the pulley to the shaft, preferably are provided not at one location, but at plural locations. In the present embodiment, each pulley is fixed to the shaft using the two pulley fastening screws, i.e., 13a, 13b or 14a, 14b.

Since the ultrasonic probe is used by being held by an operator's hand or inserted into a body cavity of the subject, the probe preferably is small and light. In order to configure the ultrasonic probe smaller and lighter, the belt 9 is formed to have substantially the same width as the swing shaft pulley 5 and the output shaft pulley 8. Therefore, screw holes 15, 16 of the pulley fastening screws 13, 14, each fixing the pulley to the shaft, are provided on circumferential surfaces of the pulleys, i.e., at positions on which the belt 9 is placed.

Of the pulley fastening screws 13a, 13b that fix the swing shaft pulley 5 to the swing shaft 4, the pulley fastening screw 13b shares its screw hole 15b with the belt fixing screw 11 that fixes the belt 9 to the swing shaft pulley 5. In other words, in the screw hole 15b, the pulley fastening screw 13b is inserted deeply in the screw hole and the belt fixing screw 11 is inserted in a position from above the pulley fastening screw 13b to a surface of the screw hole. Similarly, of the pulley fastening screws 14a, 14b that fix the output shaft pulley 8 to the output shaft 7, the pulley fastening screw 14b shares its screw hole 16b with the belt fixing screw 12 that fixes the belt 9 to the output shaft pulley 8.

Thus, even when the screw holes 15b and 16b are formed on the circumferential surfaces of the pulleys on which the belt 9 is placed, the pulley fastening screws 13b, 14b do not contact the belt 9. Thus, the swing motion can be stabilized without damaging or the like the belt 9. Further, since the belt fixing screws 11, 12 are inserted in the screw holes 15b, 16b, respectively, so as to fix the belt 9, the belt 9 can be prevented from being damaged due to repetitive sliding contact with the edges of the screw holes. Thereby the swing motion can be stabilized.

Further, at a portion of the swing shaft pulley 5 corresponding to the through hole 10 of the belt 9, a screw hole 15a is formed that is different from the screw hole 15b shared by the belt fixing screw 11 and the pulley fastening screw 13b. In the screw hole 15a, the pulley fastening screw 13a that fixes the swing shaft pulley 5 to the swing shaft 4 is inserted. Similarly, at a portion of the output shaft pulley 8 corresponding to the through hole 10 of the belt 9, a screw hole 16a is formed that is different from the screw hole 16b shared by the belt fixing screw 12 and the pulley fastening screw 14b. In the screw hole

16a, the pulley fastening screw 14a that fixes the output shaft pulley 8 to the output shaft 7 is inserted.

With this configuration, it is possible to prevent the belt 9 from contacting the pulley fastening screws 13a, 14a and the screw holes 15a, 16a. Thus, damage or the like of the belt 9 can be suppressed. In view of this point as well, the swing motion can be stabilized, which increases the reliability of data obtained and ultrasonic images obtained by processing the data.

Especially in the present embodiment in which the metallic belt 9 is used, the possibility of the belt 9 being damaged due to overlap between the belt 9 and the pulley fastening screws 13, 14 is increased as compared with the case of using the belt 9 made of a flexible material such as rubber. Therefore, it is effective that the belt 9 can be prevented from coming into contact with the pulley fastening screws 13a, 14a and the screw holes 15a, 16a.

Although the present embodiment explains the case in which the screw not having a screw head and contained inside the screw hole (e.g., hexagon socket set screw) is used as the type of the screw of the pulley fastening screws 13a, 14a, the present invention is not limited to this case. For example, regarding the pulley fastening screws 13a, 14a not sharing the screw holes with the belt fixing screws 11, 12, it is unnecessary to limit the type of the screw. Therefore, for example, even in the case of using a screw having a protruding screw head (e.g., pan-head machine screw), an effect of preventing the belt 9 from being damaged can be obtained by setting the size of the through hole 10 formed in the belt 9 such that the belt 9 does not come into contact with the screw head.

Further, although the present embodiment explains the case in which one through hole 10 having a slot shape is formed in the belt 9, the present invention is not limited to this case. For example, two through holes 10 may be formed so as to correspond to the positions of the screw holes 15a, 16a. Even if the shape and the number of the through hole 10 are different from this case, it does not mean that the configuration departs from the present invention, as long as a difference in natural frequency can be provided between the first region 17 and the second region 18.

Further, although the present embodiment explains the case in which the two pulley fastening screws 13a, 13b or 14a, 14b are used for fixing the swing shaft pulley 5 to the swing shaft 4 or fixing the output shaft pulley 8 to the output shaft 7, two or more of the pulley fastening screws may be used. In this case, the same effect as that of the above-described configuration can be obtained by appropriately changing the shape, the size and the number of the through hole 10 of the belt 9 so as to correspond to the locations of the pulley fastening screws 13a, 14a such that the pulley fastening screws 13a, 14a do not come into contact with the belt 9.

As described above, the ultrasonic probe according to the present embodiment is capable of suppressing the occurrence of the resonance phenomenon, thereby securing the stable swing motion. Further, since the pulleys and the belt can have substantially the same width, the ultrasonic probe can be configured smaller and lighter. Further, by fixing the belt 9 to the swing shaft pulley 5 and the output shaft pulley 8 by the belt fixing screws 11 and 12, respectively, and fixing the swing shaft pulley 5 and the output shaft pulley 8 to the swing shaft 4 and the output shaft 7 by the pulley fastening screws 13a, 13b and 14a, 14b, respectively, the shafts and the pulleys can be disassembled, and thus, an adjustment and a repair can be carried out easily.

(Embodiment 2)

Figure 3A:
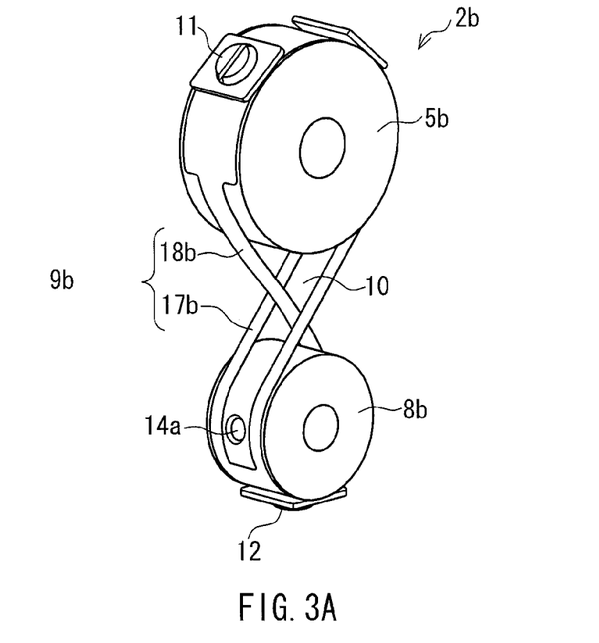
FIG. 3A is a perspective view showing a configuration of a motion transmission mechanism according to Embodiment 2 of the present invention.
Figure 3B:
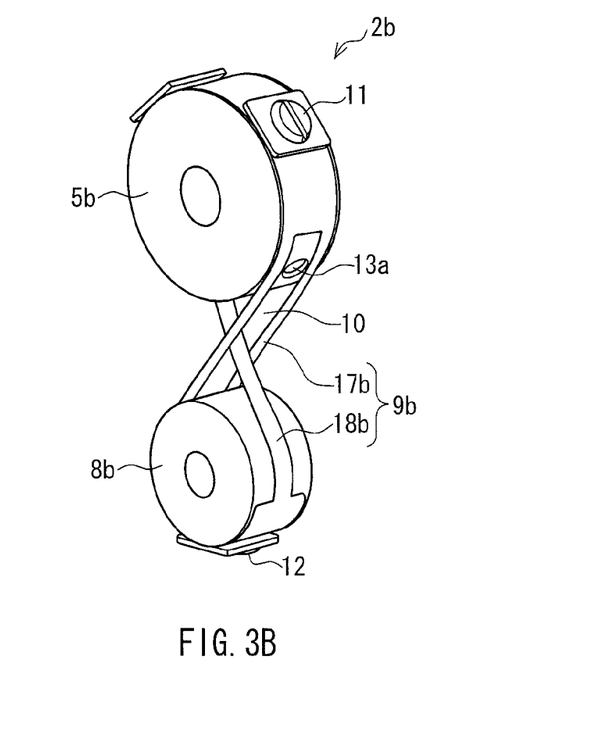
FIG. 3B is a perspective view of the motion transmission mechanism shown in FIG. 3A seen from another direction.

FIG. 3A is a perspective view showing a configuration of a motion transmission mechanism 2b of an ultrasonic probe according to Embodiment 2 of the present invention, and FIG. 3B is a perspective view of the motion transmission mechanism 2b seen from another direction. Note here that the configuration of the ultrasonic probe is identical to the configuration of the ultrasonic probe according to Embodiment 1 except for the motion transmission mechanism. Therefore, the same components as those of Embodiment 1 are denoted with the same reference numerals, and the explanation thereof will be omitted.

A swing shaft pulley 5b is formed so that a diameter of the swing shaft pulley is larger than a diameter of the output shaft pulley. When the diameter of the swing shaft pulley is assumed to a, and the diameter of the output shaft pulley is assumed to b, a torque To generated in the swing shaft pulley 5b with respect to a torque Ti applied to the output shaft pulley 8b is expressed as follows.

$$To = (a/b) \cdot Ti \quad \text{(Equation 1)}$$

With this configuration, a torque for swinging the ultrasonic transducer body (not shown) can be increased. Therefore, a small motor whose driving force is small can be used as the motor 6, whereby the ultrasonic probe further can be configured smaller and lighter.

Both ends of a belt 9b are fixed to the swing shaft pulley 5b by the belt fixing screws 11, and the vicinity of the center of the belt 9b is fixed to the output shaft pulley 8b by the belt fixing screw 12. One of the belt fixing screws 11 that fix the belt 9b to the swing shaft pulley 5b and the belt fixing screw 12 that fixes the belt 9b to the output shaft pulley 8b share their screw holes with pulley fastening screws (not shown), respectively, which is identical to Embodiment 1.

The belt 9b is composed of a first region 17b and a second region 18b connected respectively to the swing shaft pulley 5b and the output shaft pulley 8b. A through hole 10 is formed in the first region 17b. The second region 18b is formed narrower than the width of the through hole 10, and arranged so as to pass through the through hole 10. In other words, the first region 17b and the second region 18b form a cross belt configuration. Material weights of the first region 17b and the second region 18b are different from each other, whereby the first region 17b and the second region 18b have different natural frequencies.

When the belt 9b is composed of a metallic sheet material made of stainless steel for suppressing the extension of the belt 9b due to the stress applied during the swing motion of the ultrasonic transducer body 3 for example, since the belt is not as flexible as a belt composed of a rubber material such as chloroprene rubber and urethane rubber, it is difficult to form the belt 9b in the cross belt configuration by twisting. However, by utilizing the through hole 10 and by passing one end of the belt 9b through the through hole 10, the cross belt configuration can be realized easily even when the belt 9b is composed of a metallic sheet material such as stainless steel. Therefore, the cross belt configuration with respect to the pulleys can be realized easily.

By forming the belt 9b in the cross belt configuration, a contact area (contact angle) of the belt 9b with respect to the respective pulleys becomes large, which makes it possible to increase a contact friction region as compared with the case of Embodiment 1. Thus, the swing motion of the ultrasonic transducer body 3 that is performed by the repetitive forward-backward motion of the belt 9b can be stabilized further.

As described above, the ultrasonic probe according to the present embodiment has the same effect as that of the ultrasonic probe according to Embodiment 1. Further, since the motor 6 can be downsized, the ultrasonic probe further can be configured smaller and lighter.

(Embodiment 3)

Figure 4:
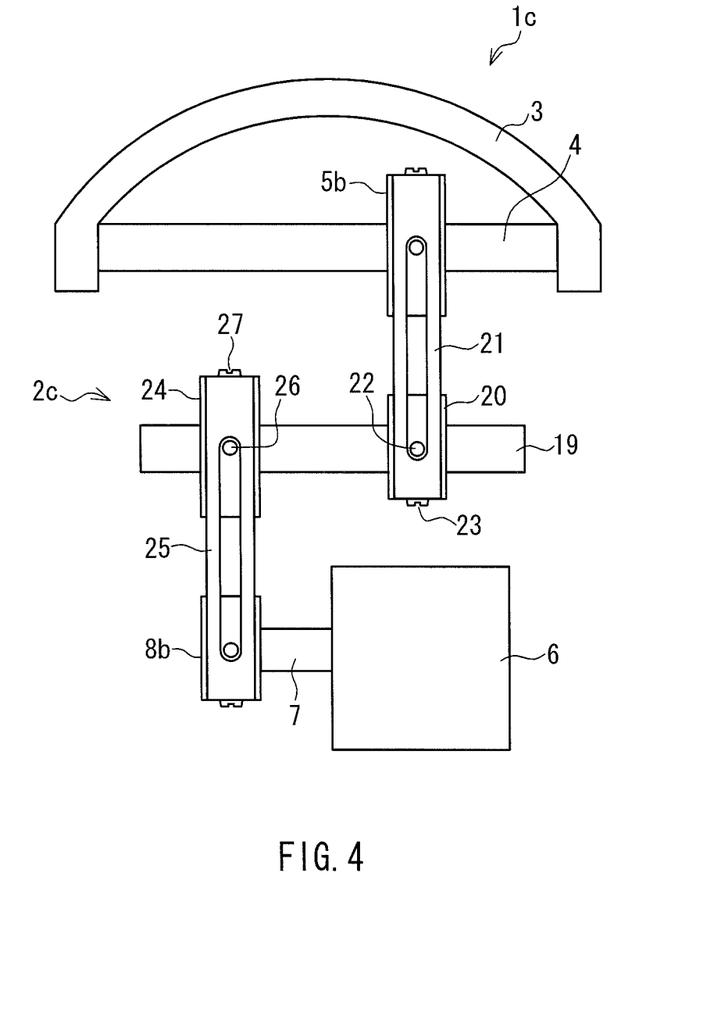
FIG. 4 is a perspective view showing a configuration of main portions of an ultrasonic probe according to Embodiment 3 of the present invention.

FIG. 4 is a side view showing a configuration of main portions inside an ultrasonic probe 1c according to Embodiment 3 of the present invention. Note here that the configuration of the ultrasonic probe is identical to the configuration of the ultrasonic probe according to Embodiment 1 except for the motion transmission mechanism. Therefore, the same components as those of Embodiment 1 are denoted with the same reference numerals, and the explanation thereof will be omitted. A motion transmission mechanism 2c according to the present embodiment has a configuration in which the driving force of the motor is transmitted by two pairs of pulleys via an intermediate shaft 19 to the swing shaft 4.

The intermediate shaft 19 is positioned between the swing shaft 4 and the output shaft 7, and supported swingably by a supporter (not shown). The intermediate shaft 19 is inserted in a first intermediate shaft pulley 20, which is fixed to the intermediate shaft 19 by a pulley fastening screw 22. A belt 21 is wound around the swing shaft pulley 5b and the first intermediate shaft pulley 20. A diameter of the first intermediate shaft pulley 20 is set so as to be smaller than a diameter of the swing shaft pulley 5b.

Further, the intermediate shaft 19 is inserted in a second intermediate shaft pulley 24, which is fixed to the intermediate shaft 19 by a pulley fastening screw 26. A belt 25 is wound around the second intermediate shaft pulley 24 and the output shaft pulley 8b. A diameter of the second intermediate shaft pulley 24 is formed so as to be larger than a diameter of the output shaft pulley 8b.

As shown in Equation 1 of Embodiment 2, regarding the driving torque of the motor 6, the rotation torque is increased by setting the diameter of the second intermediate shaft pulley 24 to be larger than the diameter of the output shaft pulley 8b. The rotation torque is increased further by setting the diameter of the swing shaft pulley 5b to be larger than the diameter of the first intermediate shaft pulley 20. In other words, the rotation torque can be increased in two stages, whereby the torque for swinging the ultrasonic transducer body 3 can be increased.

With this configuration, as compared with the motion transmission mechanism 2b according to Embodiment 2 in which the torque is increased in one stage, a difference in diameter between the pulleys can be reduced in each stage, and thus, the diameters of the pulleys themselves can be reduced. Therefore, the pulleys can be downsized, and hence a compact, easily operable ultrasonic probe can be configured along with the downsizing of the motor 6.

The two intermediate shaft pulleys, which are the first intermediate shaft pulley 20 and the second intermediate shaft pulley 24, are attached to the intermediate shaft 19. A positional relationship between the first intermediate shaft pulley 20 and the second intermediate shaft pulley 24 in a rotation direction needs to have a predetermined relationship. If the attached positions of the two intermediate shaft pulleys in the rotation direction are displaced from the predetermined relationship, the positions of the belt fixing screws 23, 27 are displaced accordingly. In that case, a deflection may occur in the belts 21, 25 during the swing motion. Consequently, the swing angle of the ultrasonic transducer body 3 is displaced.

In order to fix the first intermediate shaft pulley 20 and the second intermediate shaft pulley 24 to the intermediate shaft 19, there are, for example, a method of press-fitting or adhering the intermediate shaft to the pulleys, and a method of fixing the pulleys to the intermediate shaft using screws. When the first intermediate shaft pulley 20 and the second intermediate shaft pulley 24 are fixed to the intermediate shaft 19 by the fixing method such as the press fitting or adhesion, it is difficult to control the positional relationship between the first intermediate shaft pulley 20 and the second intermediate shaft pulley 24 in the rotation direction in the intermediate shaft 19. On the other hand, as shown in FIG. 4, when the intermediate shaft pulleys 20, 24 are fixed using the pulley fastening screws 22, 26, it is possible to regulate the positions of the intermediate shaft pulleys 20, 24 in the rotation direction by making a D-cut in advance at positions where the pulley fastening screws 22, 26 contact the intermediate shaft 19, for example. Thus, the control for the displacement can be realized easily.

When fixing the intermediate shaft pulleys 20, 24 to the intermediate shaft 19 using the pulley fastening screws 22, 26, it is necessary to suppress damage to the belts 21, 25 due to contacts between the belts 21, 25 and the pulley fastening screws 22, 26, respectively. However, by using the belts 9, 9b described in Embodiments 1, 2 as the belts 21, 25, the contacts between the belts and the pulley fastening screws can be prevented, whereby the damages of the belts can be suppressed. At the same time, the resonance state of the belts due to the rotation motion of the motor can be avoided.

Although the present embodiment explains the case in which the pulley fastening screws are used for fixing the intermediate shaft pulleys 20, 24 to the intermediate shaft 19, the pulley fastening screws are used for fixing the swing shaft pulley 5b to the swing shaft 4 and fixing the output shaft pulley 8b to the output shaft 7, which is the same as in Embodiments 1, 2.

As described above, the ultrasonic probe according to the present embodiment has a characteristic of having two pairs of the motion transmission mechanisms, at least one of which is configured such that the diameter of the pulley positioned farther in the motion transmission path when seen from the output shaft of the motor is larger than the diameter of the pulley positioned closer from the output shaft. With this configuration, the pulleys and the shafts are fixed using the fastening screws, whereby the resonance state of the belts can be prevented and the ultrasonic probe can be downsized.

Although the present embodiment explains the case in which one intermediate shaft 19 is used, the present invention is not limited to this case. Even in the case where two or more intermediate shafts 19 are used, such a configuration only increases the number of the motion transmission mechanism composed of pulleys and belts, and hence, is acceptable as long as the operability of the ultrasonic probe is not impaired.

(Embodiment 4)

Figure 5A:
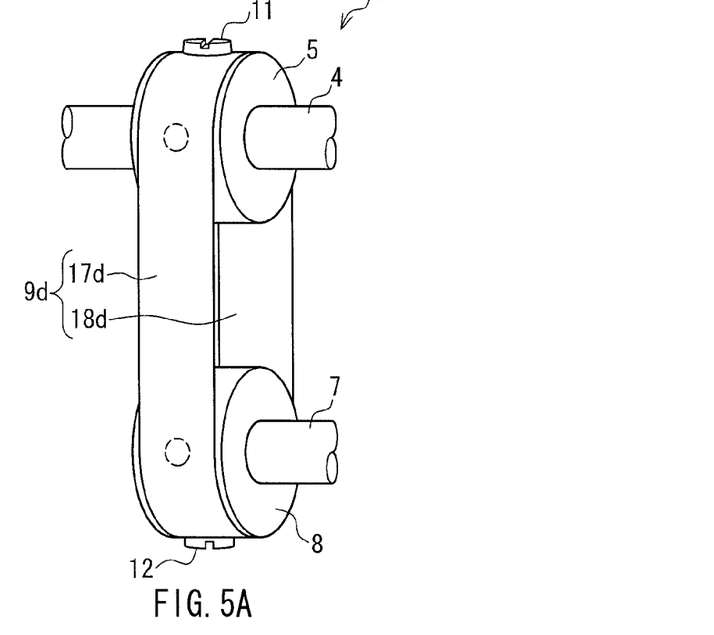
FIG. 5A is a perspective view showing a configuration of a motion transmission mechanism of an ultrasonic probe according to Embodiment 4 of the present invention.
Figure 5B:
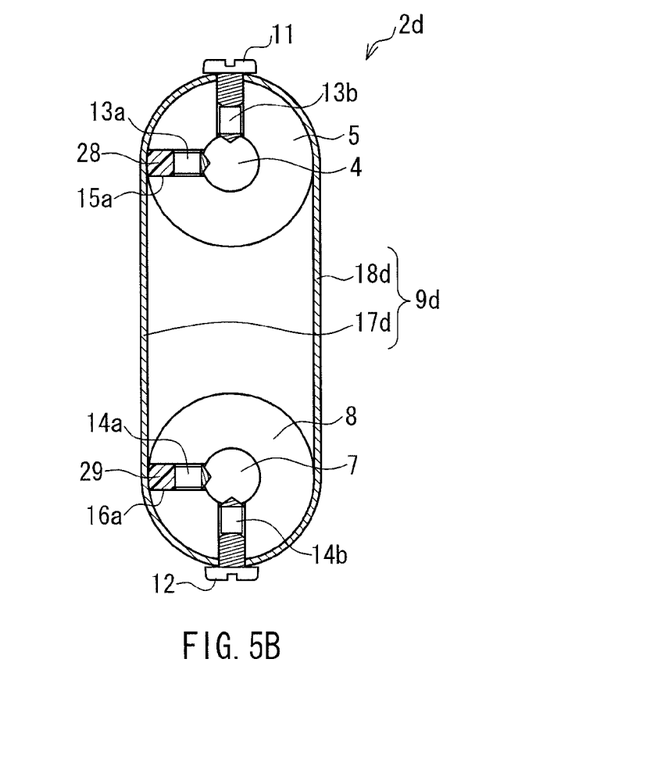
FIG. 5B is a cross-sectional view of the motion transmission mechanism shown in FIG. 5A.

FIG. 5A is a perspective view showing a configuration of a motion transmission mechanism 2d of an ultrasonic probe according to Embodiment 4 of the present invention, and FIG. 5B is a cross-sectional view of the motion transmission mechanism 2d shown in FIG. 5A. Note here that the ultrasonic probe according to the present embodiment is different from the ultrasonic probe of Embodiment 1 in that screw hole fillers 28, 29 are placed in the screw holes 15a, 15b. In the ultrasonic probe of the present embodiment, the same components as those of Embodiment 1 are denoted with the same reference numerals, and the explanation thereof will be omitted.

The screw hole fillers 28, 29 are fillers filled in the remaining spaces in the screw holes 15a, 16a to the circumferential surfaces of the pulleys after the attachment of the pulley fastening screws 13a, 14a. The screw hole fillers 28, 29 are obtained by, for example, fitting a plug-like member made of a flexible material such as rubber or resin in the screw hole, or by directly pouring a material such as rubber or resin into the screw hole and thereafter curing it. Surfaces of the screw hole fillers 28, 29 are treated by post-processing, etc., so as to form substantially a continuous surface with the circumferential surface of the pulley.

Thus, by filling the screw holes 15a, 16a with the screw hole fillers 28, 29, the belt 9d can avoid loads and damage even if the belt 9d comes into sliding contact with the screw holes 15a, 16a when placed thereon. Thereby, the swing motion can be stabilized.

In the present embodiment, the belt 9d need not be formed with a through hole such as that formed in the belt 9 in Embodiment 1. However, it is essentially necessary to differentiate the natural frequency between the two regions in the belt 9d, and a through hole may be formed. Further, the two regions in the belt 9d may be different in density and weight by partially changing the thickness of the material, partially plating the belt 9d, or partially welding/adhering an other component to the belt 9d, etc., without forming a through hole in the belt 9d.

Note here that the configuration of providing the screw hole filler in the screw hole in the present embodiment may be applied to the other embodiments described above and to the intermediate shaft pulleys in FIG. 4.

(Embodiment 5)

Figure 6:
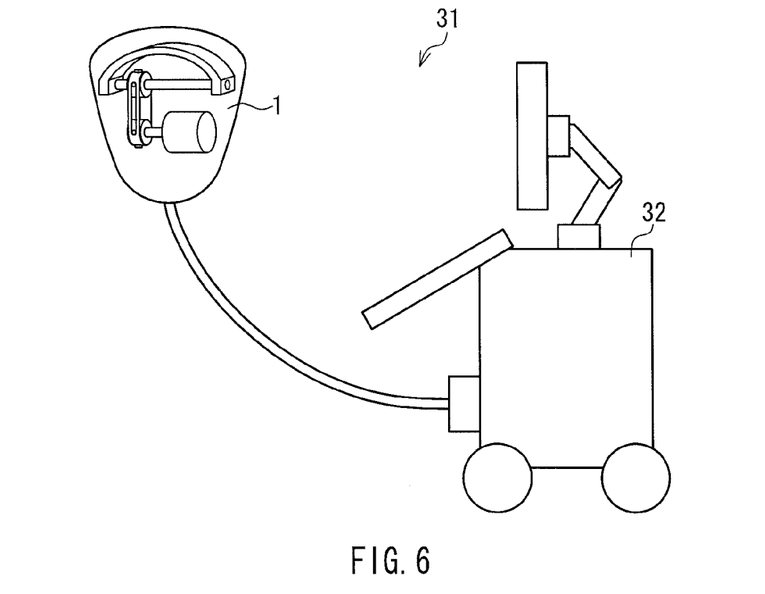
FIG. 6 is a schematic view showing a configuration of an ultrasonic diagnostic equipment according to Embodiment 5 of the present invention.

FIG. 6 is a schematic view showing a configuration of an ultrasonic diagnostic equipment 31 according to Embodiment 5 of the present invention. The ultrasonic diagnostic equipment 31 includes an ultrasonic diagnostic equipment main body 32 and an ultrasonic probe 1 that is connected electrically to the ultrasonic diagnostic equipment main body 32.

Next, the operation of the ultrasonic diagnostic equipment 31 will be described. First, an operator brings an ultrasonic wave sending/receiving face of the ultrasonic probe 1 into contact with a body surface of a subject (not shown). Next, electrical signals (driving signals) are transmitted from the ultrasonic diagnostic equipment main body 32 to the ultrasonic probe 1. The driving signals are converted into ultrasonic waves in piezoelectric transducers in the ultrasonic probe 1 so as to be transmitted to the subject (not shown). The ultrasonic waves are reflected in a body of the subject (not shown). A part of the reflected waves are received by the piezoelectric transducers in the ultrasonic probe 1, and converted into electric signals (reception signals). The converted electric signals are input in the ultrasonic diagnostic equipment main body 32, subjected to signal processing in the ultrasonic diagnostic equipment main body 32, and output to a display device such as CRT as, for example, a tomographic image.

In the ultrasonic diagnostic equipment described above, the ultrasonic probes described in Embodiments 1 to 4 are used as the ultrasonic probe 1. According to such an ultrasonic diagnostic equipment, the effects of the ultrasonic probes described in Embodiments 1 to 4 can be obtained, whereby excellent ultrasonic diagnostic images can be obtained efficiently.

Embodiments 1 to 4 explain the ultrasonic transducer body 3 in which a plurality of piezoelectric transducers are arranged in a convex shape. However, the present invention is not limited to this case. For example, the ultrasonic transducer body 3 may be one in which the plurality of piezoelectric transducers are arranged in a flat linear shape, and may be one composed of one piezoelectric transducer, not the plurality of piezoelectric transducers. The number and the arrangement of the piezoelectric transducers possessed by the ultrasonic transducer body 3 are not limited.

Industrial Applicability

The ultrasonic probe according to the present invention has an effect of increasing reliability by suppressing the resonance of a belt, and therefore, is useful in medical fields such as an ultrasonic diagnosis, a treatment and the like.

Description of Reference Numerals 1, 1c ultrasonic probe
2, 2b, 2c, 2d motion transmission mechanism
3 ultrasonic transducer body
4 swing shaft
5 swing shaft pulley
6 motor
7 output shaft
8 output shaft pulley
9, 9b, 9d, 22, 26 belt
10 through hole
11, 12, 23, 27 belt fixing screw
13a, 13b, 14a, 14b, 22, 26 pulley fastening screw
15a, 15b, 16a, 16b screw hole
17, 17b, 17d first region
18, 18b, 18d second region
19 intermediate shaft
20 first intermediate shaft pulley
24 second intermediate shaft pulley
28, 29 screw hole filler
31 ultrasonic diagnostic equipment
32 ultrasonic diagnostic equipment main body

The invention claimed is:

1. An ultrasonic probe, comprising:
an ultrasonic transducer body that transmits and receives an ultrasonic wave;
a swing shaft attached to the ultrasonic transducer body;
a motor that generates a reciprocating movement, the motor comprising an output shaft;
a pulley assembly that transmits the reciprocating movement generated by the motor from the output shaft to the swing shaft, thereby causing the ultrasonic transducer body to swing back and forth, the pulley assembly comprising:
   a first driving pulley attached to the output shaft;
   a first driven pulley that receives the reciprocating movement of the output shaft from the first driving pulley to the first driven pulley and transmits the movement to the swing shaft; and
   a first belt wrapped around the first driving pulley and the first driven pulley to transmit the reciprocating movement, the first belt including a first free side belt region extending between the first driving pulley and the first driven pulley, and a second free side belt region extending between the first driving pulley and the first driven pulley;
wherein the first and second free side belt regions are separated in the longitudinal direction of the first belt and the first and second free side belt regions have different natural frequencies so as to avoid a resonance phenomenon being established in the first belt,
wherein a through hole is formed in one of the first free side belt region and the second free side belt region to obtain different weight of the first side belt region and the second free side belt region, and the different natural frequencies are obtained by differentiating the weight of the first free side belt region and the second free side belt region.

2. The ultrasonic probe according to claim 1, wherein the pulley assembly further comprises:
an intermediate shaft that transmits the reciprocating movement of the output shaft to the swing shaft, the first driven pulley being attached to the intermediate shaft to allow the reciprocating movement to be transmitted from the output shaft to the intermediate shaft;

a second driving pulley attached to the intermediate shaft to transmit the reciprocating movement from the intermediate shaft to the swing shaft;

a second driven pulley that receives the reciprocating movement from the intermediate shaft and transmits the movement to the swing shaft; and a second belt wrapped around the second driving pulley and the second driven pulley.

3. The ultrasonic probe according to claim 1, further comprising a pulley fastening screw that attaches one of the pulleys to the respective shaft to which the pulley is attached, wherein the pulley fastening screw is inserted completely in a screw hole formed in the respective pulley, a first end of the pulley fastening screw is in contact with the respective pulley, and a second end of the screw opposite to the first end is positioned within the screw hole, and a screw hole filler is placed over the pulley fastening screw and inside the screw hole so as to fill the screw hole.

4. The ultrasonic probe according to claim 1, wherein the through hole is formed in the first free side belt region and the second free side belt region passes through the through hole.

5. The ultrasonic probe according to claim 1, further comprising a pulley fastening screw that attaches each of the pulleys to the shaft to which the pulley is attached, wherein the through hole extends along a length of the first belt, thereby permitting the pulley fastening screw to be positioned under the through hole.

6. The ultrasonic probe according to claim 5, wherein the pulley fastening screw is inserted completely in a screw hole formed in the respective pulley, and a first end of the pulley fastening screw is in contact with the respective pulley, and a second end of the screw opposite to the first end is positioned within the screw hole, and a screw hole filler is placed over the pulley fastening screw and inside the screw hole so as to fill the screw hole.

7. The ultrasonic probe according to claim 1, further comprising at least one belt fixing screw that attaches the first belt to one of the first driving pulley and the first driven pulley.

8. The ultrasonic probe according to claim 5, wherein a width of each of the pulleys is the same as a width of the belt.

9. An ultrasonic diagnostic equipment, comprising:

the ultrasonic probe according to claim 1; and an ultrasonic diagnostic equipment main body connected electrically to the ultrasonic probe, the ultrasonic diagnostic eguipment main body includes a monitor, and is configured to send driving signals to the probe and receive reception signals from the probe.

10. The ultrasonic probe according to claim 2, wherein the second belt includes a third free side belt region extending between the second driving pulley and the second driven pulley, and a fourth free side belt region extending between the second driving pulley and the second driven pulley, wherein the third and fourth free side belt regions are separated in the longitudinal direction of the second belt and the third and the fourth free side belt regions have different natural frequencies so as to avoid a resonance phenomenon being established in the second belt.

11. The ultrasonic probe according to claim 10, wherein a material weight of the third free side belt region is different from a material weight of the fourth free side belt region to obtain the different natural frequencies.

12. The ultrasonic probe according to claim 10, wherein a through hole is formed in at least one of the third free side belt region and the fourth free side belt region to obtain the different natural frequencies.

13. The ultrasonic probe according to claim 12, wherein the through hole is formed in the third free side belt region and the fourth free side belt region passes through the through hole.

14. The ultrasonic probe according to claim 13, further comprising a pulley fastening screw that attaches each of the pulleys to the shaft to which the pulley is attached, wherein the through hole extends along a length the second belt, thereby permitting the pulley fastening screw to be positioned under the through hole.

15. The ultrasonic probe according to claim 10, further comprising at least one belt fixing screw that attaches the second belt to one of the second driving pulley and the second driven pulley.

16. The ultrasonic probe according to claim 15, further comprising a pulley fastening screw that attaches each of the pulleys to the shaft to which the pulley is attached, the pulley fastening screw being inserted in a bottom of a screw hole where the belt fixing screw is received.

17. The ultrasonic probe according to claim 1, wherein the first driven pulley is fixed to the swing shaft.

18. The ultrasonic probe according to claim 7, further comprising a pulley fastening screw that attaches one of the pulleys to the respective shaft to which the pulley is attached, the pulley fastening screw being inserted in a bottom of a screw hole where the belt fixing screw is received.

19. The ultrasonic probe according to claim 2, wherein the second driven pulley is fixed to the swing shaft.

20. The ultrasonic probe according to claim 1, wherein each of the first free side belt region and the second free side belt region extend between the first driving ulley and the first driven pulley without connection to or carrying any further components.

* * * * *